US010733615B2

(12) United States Patent
Koh et al.

(10) Patent No.: US 10,733,615 B2
(45) Date of Patent: Aug. 4, 2020

(54) METHOD AND SYSTEM FOR CERTIFICATION AND VERIFICATION OF GEMSTONES (71) Applicant: Caratell PTE LTD, Singapore (SG)

(72) Inventors: Thong Hee Koh, Singapore (SG); Siow Lee Teng, Singapore (SG)

(73) Assignee: CARATELL PTE LTD, Singapore (SG)

( * ) Notice: Subject to any disclaimer, the term of this patent is extended or adjusted under 35 U.S.C. 154(b) by 439 days.

(21) Appl. No.: 14/911,724

(22) PCT Filed: Aug. 6, 2014

(86) PCT No.: PCT/SG2014/000374
§ 371 (c)(1),
(2) Date: Feb. 11, 2016

(87) PCT Pub. No.: WO2015/023230
PCT Pub. Date: Feb. 19, 2015

(65) Prior Publication Data
US 2016/0203495 A1 Jul. 14, 2016

(30) Foreign Application Priority Data

Aug. 12, 2013 (SG) .............................. 2013060850

(51) Int. Cl.
G06Q 30/00 (2012.01)
G06T 3/40 (2006.01)
(Continued)

(52) U.S. Cl.
CPC ......... *G06Q 30/018* (2013.01); *G01N 33/381* (2013.01); *G06F 16/51* (2019.01);
(Continued)

(58) Field of Classification Search
CPC combination set(s) only.
See application file for complete search history.

(56) References Cited

U.S. PATENT DOCUMENTS 3,947,120 A * 3/1976 Bar-Issac ............... G01N 21/87
356/30
4,049,350 A * 9/1977 Bruck .................... G01N 21/88
356/30
(Continued)

FOREIGN PATENT DOCUMENTS

TW          I486575 B  *  9/2013   ............. G06F 16/58
WO       1994029817 A1    12/1994
WO       2005082078 A2     9/2005

OTHER PUBLICATIONS

Paul W. Fieguth and Riyan Wan, Fast Retrieval Methods of Images with Significant Variations, Jan. 1, 2000, pp. 522-525 (Year: 2000).*
(Continued)

*Primary Examiner* — Minnah L Seoh
*Assistant Examiner* — Debra L Glennie
(74) *Attorney, Agent, or Firm* — Loeb & Loeb LLP (57) ABSTRACT The present invention discloses a method and system for certifying and verifying gemstones and a document certifying and verifying gemstones. The method comprises the steps of capturing at least one image of an inclusion in a gemstone; storing the image in a first database; and displaying the image on a certification document for presenting to a consumer, wherein the image is of sufficient magnification to allow the consumer to compare the image on the document to the gemstone viewed through an optical device to determine if the gemstone matches the image.

10 Claims, 4 Drawing Sheets (51) Int. Cl.
  *G06F 16/51* (2019.01)
  *G06Q 10/06* (2012.01)
  *G01N 33/38* (2006.01)
  *G06T 7/00* (2017.01)
  *G01N 21/87* (2006.01)

(52) U.S. Cl.
  CPC .............. *G06Q 10/06* (2013.01); *G06T 3/40* (2013.01); *G06T 7/0002* (2013.01); *G01N 21/87* (2013.01)

(56) References Cited

U.S. PATENT DOCUMENTS

| | | | | |
|---|---|---|---|---|
| 4,125,770 | A * | 11/1978 | Lang | B01J 3/062 356/30 |
| 4,162,125 | A * | 7/1979 | Schmidt | G01N 21/88 356/239.1 |
| 4,316,385 | A * | 2/1982 | DeVries | G01N 33/381 356/30 |
| 4,900,147 | A * | 2/1990 | Bowley | G01N 21/65 356/30 |
| 5,124,935 | A * | 6/1992 | Wallner | G06K 9/00 347/225 |
| 5,379,102 | A * | 1/1995 | Takeuchi | G01D 21/02 356/30 |
| 5,430,538 | A | 7/1995 | Kobayashi | |
| 5,521,984 | A * | 5/1996 | Denenberg | G06K 9/00134 382/100 |
| 5,573,684 | A * | 11/1996 | Winston | B28D 5/00 219/121.69 |
| 5,615,005 | A * | 3/1997 | Valente | G01J 3/0251 356/30 |
| 5,828,405 | A * | 10/1998 | Vanier | G01N 21/87 348/61 |
| 5,899,503 | A * | 5/1999 | Yoshizawa | B42D 15/0033 283/70 |
| 5,974,150 | A * | 10/1999 | Kaish | G06K 19/086 283/85 |
| 6,020,954 | A * | 2/2000 | Aggarwal | G01N 21/87 356/30 |
| 6,239,867 | B1 * | 5/2001 | Aggarwal | G01N 21/87 356/30 |
| 6,996,543 | B1 * | 2/2006 | Coppersmith | G06Q 10/087 235/385 |
| 7,414,709 | B2 | 8/2008 | Wagner et al. | |
| 7,461,017 | B2 * | 12/2008 | Yeko, Sr. | G06Q 30/0613 705/26.41 |
| 7,856,137 | B2 * | 12/2010 | Yonezawa | G06K 9/00899 194/328 |
| 8,255,289 | B2 | 8/2012 | Braunwart | |
| 8,270,719 | B2 * | 9/2012 | Ellawand | G01N 21/41 356/30 |
| 8,402,066 | B2 * | 3/2013 | Verboven | G01N 21/87 707/802 |
| 8,699,022 | B2 * | 4/2014 | McManus | G01N 21/718 356/306 |
| 9,222,893 | B2 * | 12/2015 | Hornabrook | G01N 21/87 |
| 2003/0002051 | A1 * | 1/2003 | Cohn | G01B 11/2545 356/601 |
| 2003/0112422 | A1 * | 6/2003 | Lapa | G01N 21/87 356/30 |
| 2003/0223054 | A1 * | 12/2003 | Warwick | G01N 21/87 356/30 |
| 2004/0072137 | A1 * | 4/2004 | Lapa | G09B 5/02 434/386 |
| 2004/0112087 | A1 * | 6/2004 | Bishop | G01N 21/87 63/32 |
| 2005/0117145 | A1 * | 6/2005 | Altman | G01N 21/87 356/30 |
| 2005/0137882 | A1 * | 6/2005 | Cameron | G06Q 30/0185 705/318 |
| 2005/0187831 | A1 * | 8/2005 | Gershburg | G06Q 10/087 705/27.2 |
| 2006/0020524 | A1 * | 1/2006 | Yeko | G06Q 30/0613 705/26.62 |
| 2006/0062446 | A1 * | 3/2006 | Porat | G01B 11/24 382/154 |
| 2006/0164623 | A1 * | 7/2006 | Wagner | G01N 21/87 356/30 |
| 2006/0196858 | A1 * | 9/2006 | Barron | B23K 26/03 219/121.69 |
| 2007/0038530 | A1 | 2/2007 | Wagner | |
| 2007/0067178 | A1 * | 3/2007 | Reinitz | G01N 21/87 705/306 |
| 2007/0132845 | A1 * | 6/2007 | Gottesman | G01N 21/87 348/143 |
| 2007/0136085 | A1 | 6/2007 | Wagner | |
| 2007/0148374 | A1 * | 6/2007 | Twitchen | A44C 17/00 428/29 |
| 2008/0000885 | A1 * | 1/2008 | Kaplan | B23K 26/032 219/121.68 |
| 2008/0143476 | A1 * | 6/2008 | Kwok | G06K 19/07758 340/5.8 |
| 2008/0230402 | A1 * | 9/2008 | Macor | G06Q 30/018 206/0.81 |
| 2008/0231833 | A1 * | 9/2008 | Shlezinger | G01N 21/15 356/30 |
| 2009/0070273 | A1 * | 3/2009 | Moryto | G06Q 10/087 705/80 |
| 2009/0125435 | A1 * | 5/2009 | Cohen | G06Q 30/06 705/37 |
| 2009/0147241 | A1 * | 6/2009 | Shlezinger | G01N 21/87 356/30 |
| 2009/0234754 | A1 * | 9/2009 | Lapa | G06Q 30/0278 705/26.1 |
| 2009/0269702 | A1 * | 10/2009 | Garabedian | A44C 17/00 430/290 |
| 2010/0121769 | A1 * | 5/2010 | Yeko, Sr. | G06Q 30/0185 705/318 |
| 2010/0250201 | A1 * | 9/2010 | Sivovolenko | G01N 21/87 703/1 |
| 2011/0310246 | A1 * | 12/2011 | Hornabrook | G01N 21/87 348/142 |
| 2012/0007971 | A1 * | 1/2012 | Schnitzer | G01N 33/381 348/61 |
| 2012/0013734 | A1 * | 1/2012 | Ranieri | G01J 3/02 348/125 |
| 2012/0274751 | A1 * | 11/2012 | Smith | G01N 21/87 348/52 |
| 2012/0323586 | A1 * | 12/2012 | Davidov | G06Q 30/0623 705/1.1 |
| 2013/0010280 | A1 * | 1/2013 | Palmieri | G01N 21/87 356/30 |
| 2013/0085792 | A1 * | 4/2013 | Klein | G06Q 30/0621 705/7.14 |
| 2013/0204736 | A1 * | 8/2013 | Klein | G06Q 30/0613 705/26.5 |
| 2014/0297368 | A1 * | 10/2014 | Ferder | G06Q 30/0206 705/7.35 |

OTHER PUBLICATIONS

Australian Patent Office, Patent Examination Report No. 1, dated Dec. 23, 2015 in corresponding Australian Patent Application No. 2014307156, 3 pages.
Australian Patent Office, Patent Examination Report No. 2, dated Feb. 17, 2016 in corresponding Australian Patent Application No. 2014307156; 5 pages.
Australian Patent Office, Patent Examination Report No. 3, dated Jun. 21, 2016 in corresponding Australian Patent Application No. 2014307156, 4 pages.
Response to Patent Examination Report No. 1, dated Jan. 20, 2016 in corresponding Australian Patent Application No. 2014307156, 15 pages.

(56) References Cited

OTHER PUBLICATIONS

Response to Patent Examination Report No. 2, dated May 20, 2016 in corresponding Australian Patent Application No. 2014307156, 18 pages.

* cited by examiner

METHOD AND SYSTEM FOR CERTIFICATION AND VERIFICATION OF GEMSTONES

FIELD OF THE INVENTION

The present invention discloses a method and system for certifying and verifying gemstones.

BACKGROUND TO THE INVENTION

It is known to provide a certificate to identify and certify a gemstone. Such certificates are often provided at the time of sale by a jeweller, but can also be provided at other times by independent gemstone certification laboratories.

Examples of certification laboratories include:
GRS (Gem Research SwissLab)
SSEF (Swiss Foundation for Gemstone Research)
Gubelin (Gubelin Gem Lab)
GIA (Gemmological Institute of America)
NGI (Nan Yang Gemmological Institute)
IGI (International Gemmological Institute)
HRD (HRD Antwerp Institute of Gemmology)
EGL (European Gemmological Laboratories).

Conventionally, gem certificates identify the gemstone through a series of written description in respect of the cut, colour and shape of the gemstone, and its size or measurement. Although this is helpful, it is not entirely accurate, as the accuracy is dependent on the author of the description at the time the certificate is produced. Some certificates also provide a photograph of the gemstone being certified.

Many gemstones can appear to have the same cut, colour, shape and even size or measurement. Therefore, when a customer gives his/her gemstone to a jeweller for assessment or repair, cleaning, resetting or re-designing, there is a chance that it can be swapped for a lesser gemstone with the same outward appearance and clarity without the customer knowing.

Inside each gemstone there are internal features, known as 'inclusions', which are unique and individual to each gemstone. Inclusions are usually other minerals or rocks present in the gemstone, but may also be water, gas or petroleum. These inclusions are likened to the gemstone's personal DNA or fingerprint.

Coloured gemstone certification in some cases provide written descriptions of internal and external features in the gemstone, for example, under a heading of 'Observations'. Some certificates will also plot such features in the form of a diagram and this is included in the certificate issued. Often these descriptions and diagrams are too technical for a lay-person to understand, adding to the uncertainty of whether a particular gemstone has been swapped by a jeweller.

It is an object of the present invention to enhance the certification credibility and accuracy of gemstone verification.

SUMMARY OF THE INVENTION

Broadly, the present invention uses imaging technology to photograph gemstone inclusions and display the inclusion image on a gemstone certificate or document.

In one form, there is provided a method for certifying and verifying gemstones, including the steps of capturing at least one image of an internal inclusion within a gemstone using a first magnification device; storing the image in a first database; and displaying the image on a certification document for presenting to a consumer, wherein the image is of sufficient magnification to allow the consumer to compare the image on the document to the gemstone viewed through a second magnification device to verify if the gemstone matches the image.

In a second form, there is provided a system for certifying and verifying gemstones, including: a first magnification device for capturing at least one image of an internal inclusion in a gemstone; a first database for storing the image; and a processor for processing the image for displaying on a certification document for presenting to a consumer, wherein the image is of sufficient magnification to allow the consumer to compare the image on the document to the gemstone viewed through a second magnification device to verify if the gemstone matches the image.

In a third form, there is provided a document certifying gemstones comprising at least one image of an internal inclusion within a gemstone, using a first magnification device, wherein the image is of sufficient magnification to allow a consumer to compare the image on the document to the gemstone viewed through a second magnification device to verify if the gemstone matches the image.

A software product for carrying out the steps of the method is also provided.

The location of the inclusion may be identified using an x, y, z axis and displayed on the document. This enhances the credibility and accuracy of the certification and verification.

The magnification level may also be displayed on the document. This makes it easier for a consumer verifying the gemstone to set the correct magnification on his/her microscope to accurately view the inclusion. Preferably, the magnification level range is between 10 and 100 times, depending on the clarity of the gemstone.

Additional physical identification data may also be displayed on the document for added credibility and accuracy, including one or more of the gemstone's appearance, shape, size, weight, measurements, colour, refractive index, specific gravity and absorption spectrum.

To allow a consumer to access the document in real-time, for example upon purchasing a gemstone or receiving his/her returned gemstone from a jeweller, the document may be stored in a second database (which may comprise one database together with the first database) wherein the second database is accessible by a consumer via a smartphone application or online web application for displaying the stored document on the consumer's smartphone or computer in real-time.

Examples of inclusions which may be imaged in this invention include one or more of solid, liquid or gas inclusions, zones of crystal growth, striation, healed fractures, hollow growth tubes, needle-shaped crystals, twin-planes, internal fissures, cleavages, stress cracks, doubling effect, bubbles, cleavage fault, curved striae, dark ball like inclusions, feather, fingerprint, flash effect, halo inclusions, internal growth patterns, liquid filled or healing feathers, needle or feather inclusions, rain inclusions, swirl marks, three-phase inclusions, tube inclusions, twinning planes, colour zone and two-phase inclusions.

Forms of the present invention allow customers to recognise their own gemstone's DNA (such as its cut, colour, shape, size or measurement, internal inclusions) through visual recognition and specialized high definition microscopic photography. The gemstone's internal and external features are visually captured and crystallized in photographs taken using high definition optical devices. The details and photographs are placed on the gemstone document, making it simple for a customer to look at their gemstone through an optical device such as a microscope and compare to the document to check for any inconsistencies.

The invention therefore provides enhanced accuracy by removing the perennial fear that most owners of gemstones have of the possibility of the gemstone being swapped, exchanged, damaged or reduced in size or quality when sent for cleaning, repair, re-setting or re-designing. Use of simple optical devices such as microscopes makes the process easily accessible and understandable by lay-persons. The invention thereby enhances the certification credibility and accuracy of gemstone verification.

BRIEF DESCRIPTION OF THE FIGURES

An illustrative embodiment of the present invention will now be described with reference to the accompanying figures. Further features and advantages of the invention will also become apparent from the accompanying description.

DESCRIPTION OF PREFERRED EMBODIMENT

The following description is presented to enable any person skilled in the art to make and use the invention, and is provided in the context of a particular application and its requirements. Various modifications to the disclosed embodiments will be readily apparent to those skilled in the art, and the general principles defined herein may be applied to other embodiments and applications without departing from the spirit and scope of the present invention. Thus, the present invention is not intended to be limited to the embodiments shown, but is to be accorded the widest scope consistent with the principles and features disclosed herein.

Figure 1:
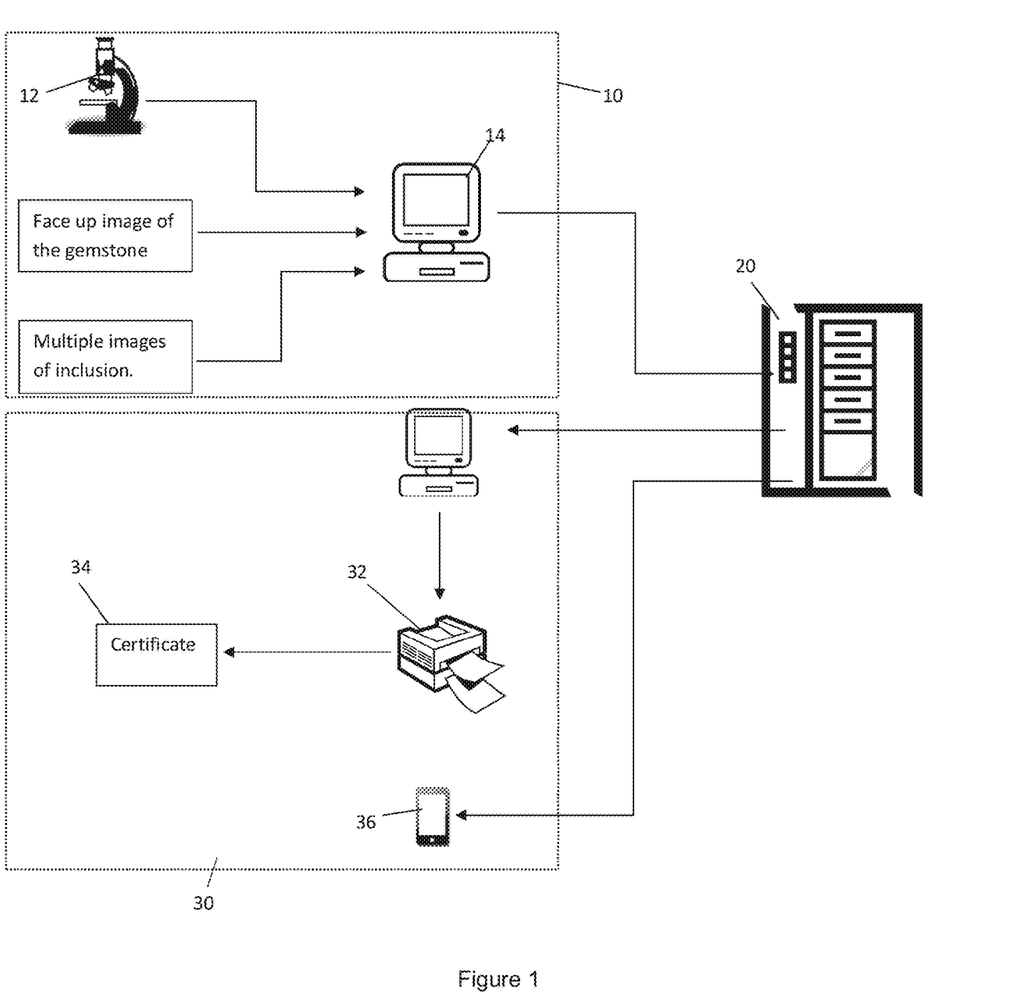
FIG. 1 is a system overview diagram of one embodiment of the system of the invention.

FIG. 1 shows an input means 10 for capturing images and details of a gemstone, comprising an optical device 12 connected to a CPU 14 running a software program. The optical device 12 may be a high definition microscope having an inbuilt camera, for example those supplied under the brands Reicher and Kruss. In some embodiments, the optical device may produce 3D or 4D images, or holograms. The images and details are processed and stored in a server/processor 20. The server/processor 20 runs a software program for creating a certificate using the stored images and details. Once the certificate has been created, output means 30 provide the certificate to the customer. The output means 30 may comprise a high resolution printer 32 for printing a hard copy certificate 34, or alternatively or in addition, a software program which may run on a CPU or a smartphone 36 for electronically displaying the certificate to the customer.

All uploaded data relating to the gemstone sent for certification shall be properly captured and saved in the server 20 for retrieval purposes as needed from time to time. Preferably, the data is accessible via a smartphone application. This allows consumers to retrieve their certification through their mobile application in real time whenever and wherever they are, should the need for them to verify their gemstone on the spot arises.

The software program collates the relevant data and computes the information/images before allocating the data and images into pre-programmed/determined fields in the certificate template. The software program may also auto generate a certification number and record the date and time of the issuance of the certificate. Once the examiner and gemmologist have verified/confirmed the accuracy of the information and data collated, the software program will auto generate the certificate with the approved data and, preferably, no further amendments/changes can be made to the certificate except via special authority from a software administrator.

Figure 2:
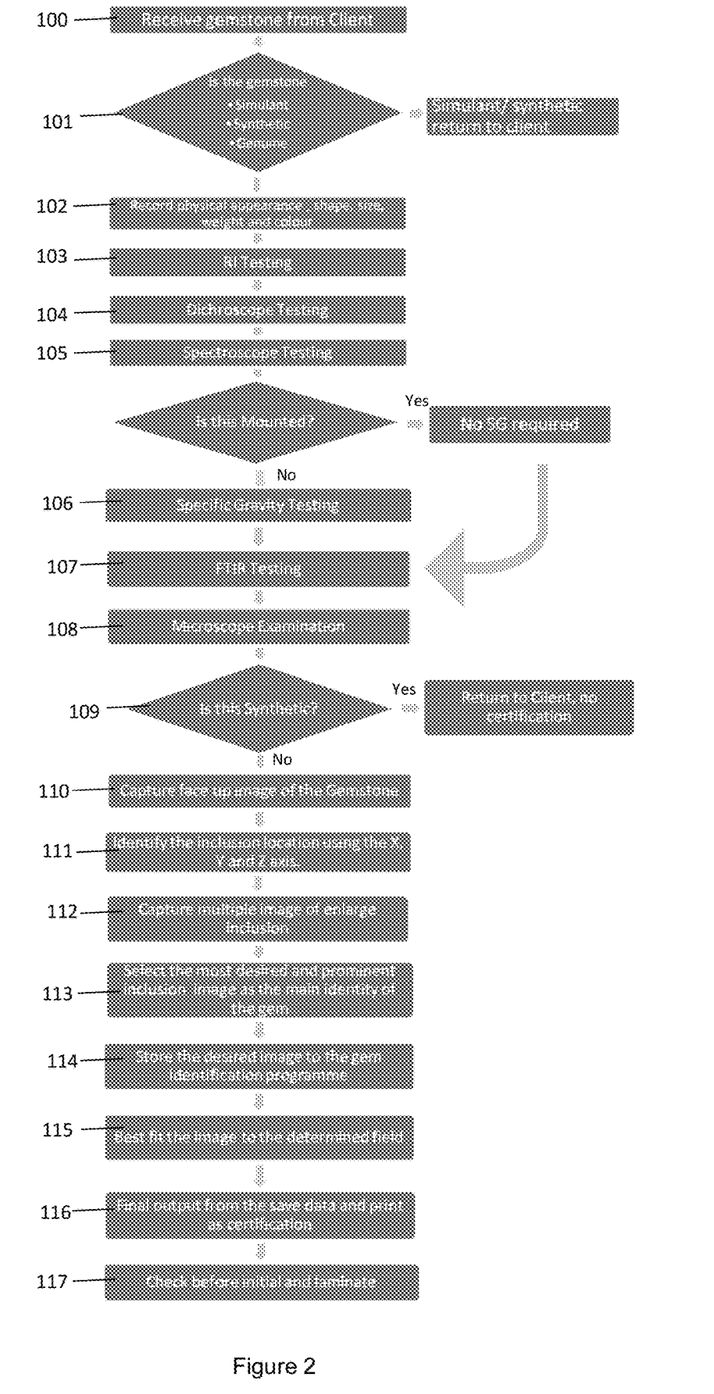
FIG. 2 is a flow diagram of one embodiment of the method of the invention.

FIG. 2 shows a flow diagram of one method of identifying and certifying gemstones. The certifier (gemmologist, jeweller or otherwise) receives a gemstone from a client 100. The gemstone may be any type of precious stone, including but not limited to coloured gemstones. The present embodiment and invention may be applied to both un-mounted loose gemstones as well as gemstones that are mounted on a piece of jewellery, as long as the image of the inclusion can be clearly captured.

The certifier determines if the gemstone is genuine 101. If the gemstone is not genuine, for example a simulant or synthetic stone, it is returned to the client. If the gemstone is genuine, then a job number will be issued and the physical characteristics of the gemstone recorded 102. The physical characteristics may include the appearance, shape, size, weight, measurements (length, width and depth) and colour.

The refractive index (RI) is then determined using a refractometer 103 which allows the certifier to determine the type of gemstone. RI is a ratio which indicates the optical density of a substance related to the angles of incidence and refraction of light.

Dichroscope testing is then performed 104 to test for pleochroism or trichroism. This test streamlines down the possibility of gemstone, sometimes it can even help to identify whether is there any treatment done on certain gemstones.

Spectroscope testing is then undertaken 105 to identify the absorption spectrum. Each variety gemstone has a unique absorption spectrum which helps to identify the gem.

If the gemstone is not mounted (for example on a ring, earring, pendant, etc.) then the specific gravity (SG) can be determined 106. The SG is the ratio of the weight of a substance to the weight of an equal volume of water. Every gem has its own SG and so the SG can be used as an additional value in gemstone identification.

Fourier Transform Infrared Spectroscopy (FTIR) testing is then undertaken 107 using an infrared spectrometer. Infrared spectrometers are used to measure absorption in materials within the infrared part of the electromagnetic spectrum. IR radiation is passed through a sample. Some of the IR is absorbed by the sample and some of it is transmitted. The resulting spectrum represents the molecular absorption and transmission, creating a molecular fingerprint of the sample. Like a fingerprint, no two unique molecular structures produce the same infrared spectrum. This makes FTIR very useful for analysis such as to:

Detect polymers, oils and resins used for impregnation, e.g. in jadeite, opal or emerald Distinguish certain natural and synthetic gem materials, e.g. emerald Opinions on heat treatment on ruby and sapphire.

A microscope examination is then performed 108. Initially, the certifier will confirm via the microscope examination that the gemstone is a genuine stone 108. If it is not genuine, then the gemstone will be returned to the client 109.

Figure 3:
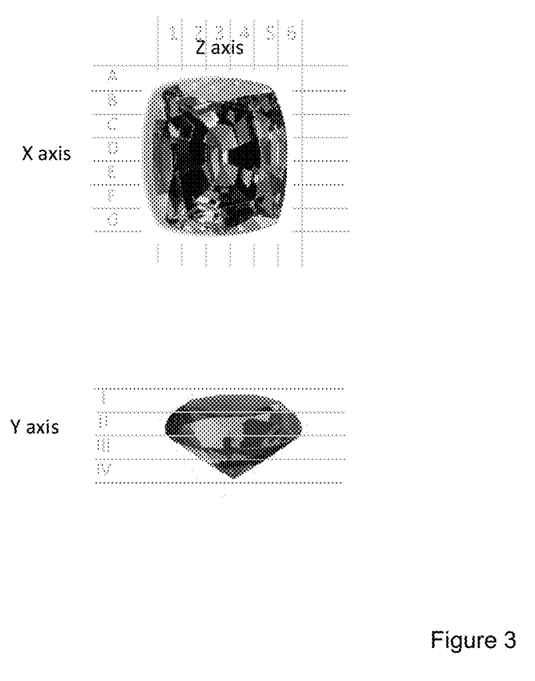
FIG. 3 shows two images illustrating an x, y, z axis determination of inclusion locations.

If it is genuine, then the microscope testing will also determine whether the stone has undergone any treatment. A face up/frontal image (top view and side/profile view) of the gemstone will then be captured 110 and saved into the system. Inclusion location(s) will then be identified 111 using the x, y, z axis as shown in FIG. 3, and saved in the system. For example, the inclusion location may be D, III, 3 (x, y, z).

Multiple images of the inclusion are then captured under the microscope 112.

The imagery may be magnified up to 100 times to ensure the inclusions are clearly seen in the images. The most desired one or two images showing the inclusion most prominently are then selected 113 to be used as the main identification of the gemstone. These images are stored to the gem identification program 114. Using the gem identification program, the selected image(s) and best fitted to the determined field 115.

Internal features or inclusions which may be microscopically determined using the above method include:

Solid, liquid or gas inclusions

Zones of crystal growth or other structural features, including colour zones and layers of inclusions, striation Healed fractures which resemble 'fingerprints' within the stone Inclusions in characteristics shapes, such as hollow growth tubes and needle-shapes crystals Twin-planes revealing change in direction of crystal structure Internal fissures, cleavages and stress cracks Evidence of treatment such as dyeing, fracture filling in ruby, oiling in emerald Doubling effect Inclusions which allow us to identify synthetic stones (such a 'flux') and stimulants (such as join marks in a doublet) curve striation Bubbles Cleavage fault Curved striae Dark ball like inclusions Feather Fingerprint Flash effect Halo inclusions Internal growth patterns Liquid filled or healing feathers Needle or feather inclusions Rain inclusions Swirl marks Three-phase inclusions Tube inclusions Twinning planes Colour zone Two-phase inclusions.

The data determined or calculated for the gemstone, together with the images, are saved to the database for processing by the gem identification program. The program then processes the saved data and images to generate a certificate 116 which includes a magnified face-up/frontal image of the gemstone together with microscopic images of the inclusions with the x, y and z axes. The certificate also includes the data collected by the certifier.

A final check on the certificate generated by the system is then performed and confirmed by a trained gemmologist who places his/her signature on the certificate 117. If the client requires a hard copy certificate, the certificate is then printed and laminated. Alternatively or in addition, an electronic copy of the certificate (preferably in an uneditable form) may be emailed or otherwise provided to the client.

Figure 4:
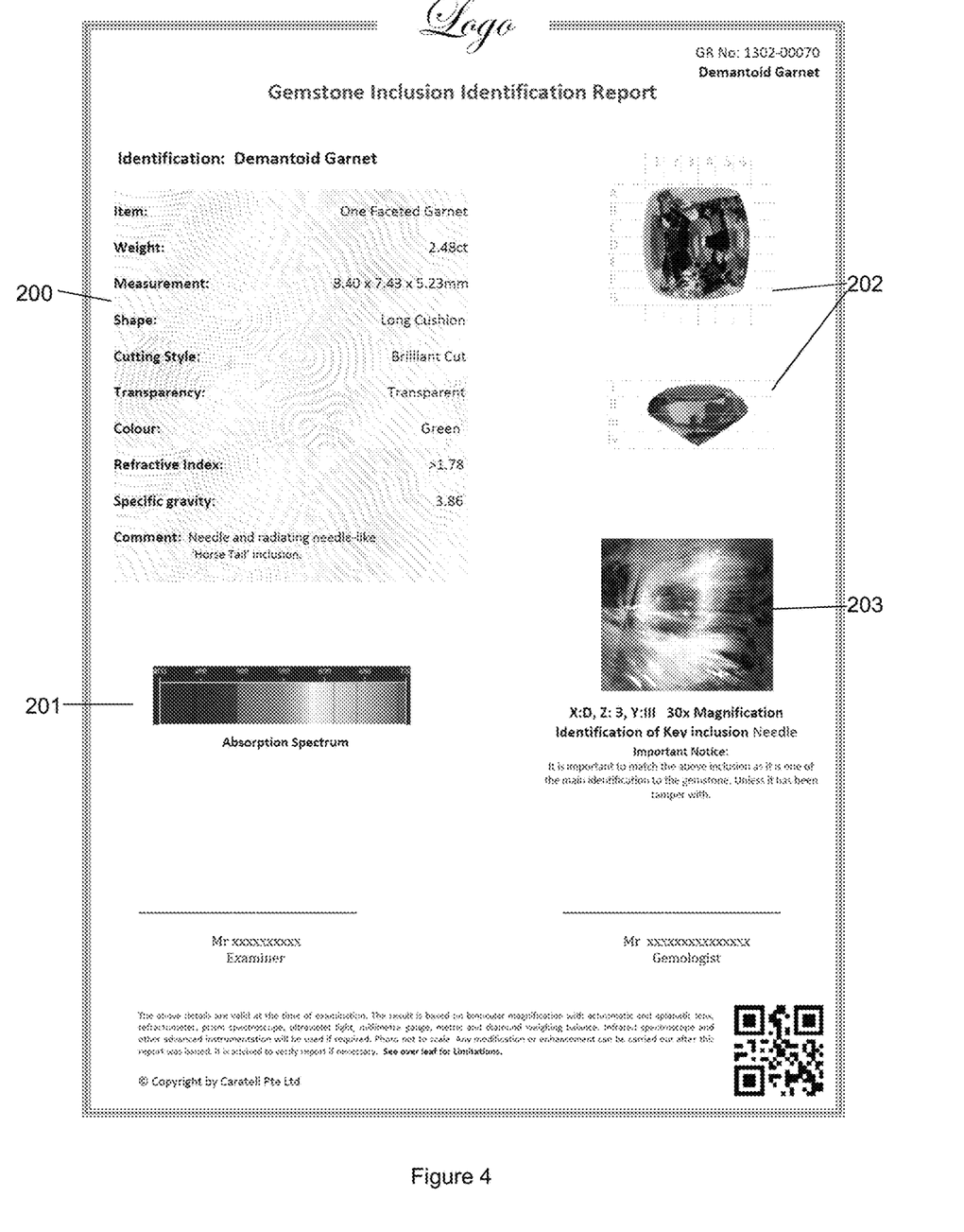
FIG. 4 is an exemplary gemstone certificate/document accordingly to one embodiment of the invention.

An exemplary certificate/document generated by the system is shown in FIG. 4. The specific details of the gemstone are listed on the left hand side of the certificate (area marked 200) and include item, weight, measurement, shape, cutting style, transparency, colour, refractive index, specific gravity, and comments. Underneath those details in the area marked 201 is the absorption spectrum. On the right hand side of the certificate (area marked 202) are the face-up (top view) and frontal (side/profile view) photographs of the gemstone, and in the area marked 203 is the microscopic image of the inclusion and its location. The photographs may be 3D, 4D, or holograms in some embodiments. The certificate may also indicate the number of times the inclusion(s) has been magnified to allow for more accurate viewing of each inclusion.

In alternative embodiments, more than one page may be used in the certificate, for example when more than one inclusion may be documented and photographed. A second (or more) page(s) may then be included with the certificate to feature the additional inclusions.

It is preferred the above processes be undertaken by qualified gemmologists to ensure the accuracy of the readings and diagnosis when it is being input into the system. This will help eliminate the possibility of misjudgement or inability to accurately locate the inclusions in the gemstone.

For added accuracy, the certificate may be cross-checked and verified by a second gemmologist before the certificate is approved and printed for signature.

To ensure the customer of authenticity, further security measures may be used on the certificate. For example, the signatures on the certificate may be done in two different coloured pens, one black, and one blue. A blind emboss of the certifier's stamp on the certificate proper with all the relevant information and photographs taken of the gemstone may also be used. Other security features that are known could also be used.

In addition to the physical details of the gemstone described above, other key or important features of each individual gemstone which may be recorded on the certificate include:

Crystal face markings, cracks, cleavage, natural, nick, pit, and fracture surfaces of rough gem material Damage—fractures, scratches, chips, etch marks, sharpness of facet edges or crystal face edges Surface condition—lustre, perfection of polish, fissures Quality of cut—polishing lines/mark, facet junctions/edge and symmetry, extra facets Grain or texture—indication by different degrees of lustre, colour or polish Detection of composite stones—joins, difference in lustre from different materials.

Using the present method it is, for example, capable of clearly identifying and showing the difference between two blue sapphires of the same size and cut since the gemstone is recorded on an 'as is' basis with all its inherent internal inclusions and external features through magnified photography of such inclusions and/or features and these are imprinted on the certificate for any person (including the owner-customer) to verify using a microscope.

The certificate goes beyond the conventional certificate where only basic information such as weight, cut style, colour, shape, size, measurements, refractive index, spectrum (if there is one) and comments on inclusions or diagrams of inclusions are shown. Accordingly, the certificate gives the customer the confidence of having a more accurate detailing of their gemstone than any other certificate currently available in the world and it removes/minimises any risk of gemstone fraud or certificate forgery.

As the certificate will be stored in the database, information can be retrieved in times of need where a duplicate certificate can be issued when one loses the original certification.

The lay-consumer (not trained in gemmology) can easily identify a gemstone by viewing and matching the microscopic image on the certificate with the actual gemstone in hand using an ordinary desktop or portable mobile clip-on magnifier. Thus verification of gemstone authenticity can be done almost immediately.

This reduces the risk of gems being swapped by unscrupulous jewellers or traders or suppliers who may wish to replace visually similar gemstones (where the weight, measurement and colour is not obvious to the untrained eye but its inherent value differing greatly) to fool/defraud the unsuspecting purchasers.

With the microscopic imagery, it is easily identifiable if the gemstone has been tampered with. For example, emerald can be oiled or the oiling process undone, if the emerald was first sent in for certification when it was free from oil, but after certification the trader may send the emerald for oil treatment to reduce the visibility of the inclusion(s) to command a higher price for the emerald. In order to verify the grading, consumers may send the emerald to any laboratory to verify the stone and the certification. So if there is a microscopic image printed on the certificate showing the emerald is free from treatment, and when the consumer retrieves the emerald to find that it has undergone treatment, he will instantly know that the emerald has been tampered with. This invention will help protect the interests of the consumer.

For gemstones that are mounted on a ring/bracelet/necklace that needs to be altered or serviced or polished, such pieces of gems have to be left with the jewellers to carry out the required services. It is difficult to verify a gemstone mounted in a jewellery setting, so consumers would simply need to base their trust on the jeweller.

The ordinary consumer can be assured that his/her gemstone handed over to the jeweller will be the same gemstone returned back to him/her by simply verifying the gemstone and the certificate on the spot with the microscope before leaving the jeweller's premises. This acts as a two-edged sword since the jeweller can also be assured that the customer having collected his/her gemstone can verify and confirm it is the same gemstone before leaving the premises.

Using a common microscope for verification purposes is easy and cost effective compared to using other laboratory equipment which most jewellers would not have on their premises.

Most consumers and jewellers would rely on the laser inscriptions to verify their purchase of diamonds. This is the common practice by international laboratories. However, such method can be easily circumvented and go undetected, since polishing the laser inscription away is possible and replacing with a lesser grade diamond or a synthetic or simulate diamond by re-inscribing the same number.

Most certification would indicate whether the gemstone has undergone a treatment, such as heat, diffusion, and lead/glass filling, but not providing physical evidence to conclude this finding. Such as the after effect on the 'inclusion' after heating that determine the treatment undergone by the gemstone. For example, if there was a micro photo image of the "inclusion" showing how the needle had 'melted' and turned into 'dust', one can then safely conclude that the gemstone had undergone heat treatment. This means that a consumer will have to simply base her trust on the laboratory's decision on what treatment the gemstone underwent, without knowing whether the laboratory has properly graded the gemstone. This may allow conspiracy between the grader and the dealer, as there is no physical photo imaging as proof to verify the state of the gemstone at the time of grading. With the proposed micro photo imaging of the "inclusions" we will be able justify and quantify the grading and so consumer will be able to have a better understanding on their gemstones and know without a doubt the quality of the gemstone they are purchasing.

The process could also be used as an added safeguard for a gemmologist who can use the system to reduce the possibility of an inadvertent mix-up of the gemstones during the grading process.

It is also envisaged that a "QR code" or similar may be used to allow consumers to verify the authenticity of a certification through an online certification check or via a smartphone application linked to the server's gemstone certification repository, before making a purchase. At the same time the consumer will be able to verify the online certification image and the micro photo imaging of the "inclusions" is the same as the physical gemstone that they are about to purchase. In addition, in the event that a customer decides to do a resetting of their gemstone with another jeweller and they forget to bring their gemstone certification, the consumer may easily retrieve online its certification and verify the micro photo image of the "inclusions" In the gemstone through a microscope.

Reference throughout this specification to 'one embodiment' or 'an embodiment' means that a particular feature, structure, or characteristic described in connection with the embodiment is included in at least one embodiment of the present invention. Thus, the appearance of the phrases 'in one embodiment' or 'in an embodiment' in various places throughout this specification are not necessarily all referring to the same embodiment.

Furthermore, the particular features, structures, or characteristics may be combined in any suitable manner in one or more combinations. It will be appreciated that persons skilled in the art could implement the present invention in different ways to the one described above, and variations may be produced without departing from its spirit and scope.

Any discussion of documents, devices, acts or knowledge in this specification is included to explain the context of the invention. It should not be taken as an admission that any of the material forms part of the prior art base or the common general knowledge in the relevant art, in any country, on or before the filing date of the patent application to which the present specification pertains.

What is claimed is:

1. A processor-implemented method for certifying and verifying gemstones, including the steps of:
   capturing at least three images of a first gemstone, wherein the at least three images include a top view, a side view, and a 10x to 100x magnified internal view of one or more internal inclusions of the first gemstone using a first microscope;
   identifying the location of a volume within the first gemstone, wherein the volume includes the one or more internal inclusions within the first gemstone, the volume is defined by an x-y-z axis of the first gemstone, the top view of the first gemstone includes a first grid defining two axes of the x-y-z axis, and the side view of the first gemstone includes a second grid defining one axis of the x-y-z axis;

storing the at least three magnified images and the location of the volume within the first gemstone that includes the one or more internal inclusions in a database;

allocating each of the at least three images to a respective field of an electronic certificate template using the processor to access the database and process the at least three images to generate an electronic certificate, the electronic certificate including the at least three images that are each allocated to the respective field of the electronic certificate template;

displaying the top view with an indication of the corresponding two axes, the side view with an indication of the corresponding one axis, the 10x to 100x magnified internal view of the one or more internal inclusions, and the location of the volume within the first gemstone that includes the one or more internal inclusions within the first gemstone to a consumer;

identifying the location of the volume within the first gemstone that includes the one or more internal inclusions within a second gemstone based on the top view that compares the top view with the indication of the corresponding two axes and the side view with the indication of the corresponding one axis; and verifying that the first gemstone and the second gemstone are the same in response to the volume within the second gemstone including the one or more internal Inclusions of the first gemstone based on the 10x to 100x magnified internal view of one or more internal inclusions of the first gemstone.

2. The method of claim 1, wherein the stored magnified image and location is displayed to a consumer on one or more of a smartphone or web application and a printed certificate.

3. The method of claim 2, further including displaying the magnification level of the magnified image.

4. The method of claim 3, further including displaying physical identification data of the first gemstone to the consumer, the physical identification data comprising one or more of the first gemstone's appearance, shape, size, weight, measurements, color, refractive index, specific gravity and absorption spectrum.

5. The method of claim 4, wherein the inclusion includes one or more of solid, liquid or gas inclusions, zones of crystal growth, striation, healed fractures, hollow growth tubes, needle-shaped crystals, twin-planes, internal fissures, cleavages, stress cracks, doubling effect, bubbles, cleavage fault, curved striae, dark ball like inclusions, feather, fingerprint, flash effect, halo inclusions, internal growth patterns, liquid filled or healing feathers, needle or feather inclusions, rain inclusions, swirl marks, three-phase inclusions, tube inclusions, twinning planes, color zone and two-phase inclusions.

6. A system for certifying and verifying gemstones, including:
  a first microscope including a processor and a memory, the memory storing instructions for execution on the processor for:
    capturing at least three images of a first gemstone, wherein the at least three images include a top view, a side view, and a 10x to 100x magnified internal view of one or more internal inclusions of a first gemstone, and
    identifying the location of a volume within the first gemstone, wherein the volume includes the one or more internal inclusions within the first gemstone, the volume is defined by an x-y-z axis of the first gemstone, the top view of the first gemstone includes a first grid defining two axes of the x-y-z axis, and the side view of the first gemstone includes a second grid defining one axis of the x-y-z axis;

storing the at least three magnified images and the location of the volume within the first gemstone that includes the one or more internal inclusions in a database;

allocating each of the at least three images to a respective field of an electronic certificate template using the processor to access the database and process the at least three images to generate an electronic certificate, the electronic certificate including the at least three images that are each allocated to the respective field of the electronic certificate template;

displaying the top view with an indication of the corresponding two axes, the side view with an indication of the corresponding one axis, the 10x to 100x magnified internal view of the one or more internal inclusions, and the location of the volume within the first gemstone that includes the one or more internal inclusions within the first gemstone to a consumer;

identifying the location of the volume within the first gemstone that Includes the one or more internal inclusions within a second gemstone based on the top view to compare the top view with the indication of the corresponding two axes and the side view with the indication of the corresponding one axis; and verifying that the first gemstone and the second gemstone are the same in response to the volume within the second gemstone including the one or more Internal inclusions of the first gemstone based on the 10x to 100x magnified internal view of one or more internal inclusions of the first gemstone.

7. The system of claim 6, wherein the stored magnified image and location is displayed to a consumer on one or more of a smartphone or web application and a printed certificate.

8. The system of claim 7, further including the processor displaying the magnification level of the magnified image.

9. The system of claim 8, further including the processor displaying physical identification data of the first gemstone to the consumer, the physical identification data comprising one or more of the first gemstone's appearance, shape, size, weight, measurements, color, refractive index, specific gravity and absorption spectrum.

10. The system of claim 9, wherein the inclusion includes one or more of solid, liquid or gas inclusions, zones of crystal growth, striation, healed fractures, hollow growth tubes, needle-shaped crystals, twin-planes, internal fissures, cleavages, stress cracks, doubling effect, bubbles, cleavage fault, curved striae, dark ball like inclusions, feather, fingerprint, flash effect, halo inclusions, internal growth patterns, liquid filled or healing feathers, needle or feather inclusions, rain inclusions, swirl marks, three-phase inclusions, tube inclusions, twinning planes, color zone and two-phase inclusions.

* * * * *